United States Patent

Jones et al.

[11] Patent Number: 5,922,911
[45] Date of Patent: Jul. 13, 1999

[54] PROCESS FOR THE MANUFACTURE OF ACETIC ANHYDRIDE

[75] Inventors: William Crawford Jones; Eleanor Hawkins Cwirko, both of Kingsport, Tenn.

[73] Assignee: Eastman Chemical Company, Kingsport, Tenn.

[21] Appl. No.: 09/066,985

[22] Filed: Apr. 24, 1998

[51] Int. Cl.$^6$ .................................................. C07C 51/54
[52] U.S. Cl. .............................................................. 562/893
[58] Field of Search ............................................. 562/893

[56] References Cited

U.S. PATENT DOCUMENTS

| | | |
|---|---|---|
| 3,927,078 | 12/1975 | Lapporte et al. . |
| 4,046,807 | 9/1977 | Kuckertz . |
| 4,115,444 | 9/1978 | Rizkalla . |
| 4,252,741 | 2/1981 | Porcellie et al. . |
| 4,374,070 | 2/1983 | Larkins et al. . |
| 4,430,273 | 2/1984 | Erpenbach et al. . |
| 4,559,183 | 12/1985 | Hewlett . |
| 5,003,104 | 3/1991 | Paulick et al. . |
| 5,292,948 | 3/1994 | Zoeller et al. . |
| 5,672,744 | 9/1997 | Kagotani et al. . |

FOREIGN PATENT DOCUMENTS

| | | |
|---|---|---|
| 0008396 | 3/1980 | European Pat. Off. . |
| 0087869 | 9/1983 | European Pat. Off. . |
| 0087870 | 9/1983 | European Pat. Off. . |
| 2315069 | 1/1998 | United Kingdom . |

*Primary Examiner*—Paul J. Killos
*Attorney, Agent, or Firm*—Matthew W. Smith; Charles R. Martin; Harry J. Gwinnell

[57] ABSTRACT

Disclosed is a carbonylation process for the manufacture of acetic anhydride wherein the utilization of carbon monoxide is increased. The process involves the liquid phase manufacture of acetic anhydride by contacting a mixture of (i) a reactant compound selected from methyl acetate, dimethyl ether or a mixture thereof, (ii) methyl iodide, (iii) catalyst components comprising rhodium and one or more promoters, and (iv) dissolved carbon monoxide in a carbonylation zone in which carbon monoxide is not fed below the surface of the mixture in a manner to increase the concentration of carbon monoxide in the liquid reaction mixture.

6 Claims, No Drawings

PROCESS FOR THE MANUFACTURE OF ACETIC ANHYDRIDE

This invention pertains to an improved carbonylation process for the manufacture of acetic anhydride wherein the utilization of carbon monoxide is increased. More specifically, this invention pertains to the liquid phase manufacture of acetic anhydride by contacting a mixture of (i) a reactant compound selected from methyl acetate, dimethyl ether or a mixture thereof, (ii) methyl iodide, (iii) catalyst components comprising rhodium and one or more promoters, and (iv) dissolved carbon monoxide in a carbonylation zone in which carbon monoxide is not fed below the surface of the mixture in a manner to increase the concentration of carbon monoxide in the liquid reaction mixture. The methyl acetate and/or dimethyl ether, methyl iodide and carbon monoxide present in the mixture react to form acetic anhydride, thereby decreasing significantly the concentration of carbon monoxide in the mixture. When the resulting reaction mixture is subjected to conventional flash distillation to separate and recover acetic anhydride, less carbon monoxide is lost from the production system.

The preparation of acetic anhydride by contacting in the liquid phase a mixture comprising methyl acetate and/or dimethyl ether and methyl iodide with carbon monoxide in the presence of a rhodium catalyst has been reported extensively in the patent literature. See, for example, U.S. Pat. Nos. 3,927,078; 4,046,807; 4,115,444; 4,252,741; 4,374,070; 4,430,273; 4,559,183; 5,003,104; and 5,292,948 and European Patents 8396; 87,869; and 87,870. These patents disclose that the reaction rate can be increased if the catalyst system includes a promoter such as certain amines and quaternary ammonium compounds, phosphines and phosphonium compounds and inorganic compounds such as alkali metal salts e.g., lithium iodide. Normally, both the reaction (process) mixture and the crude product are substantially anhydrous, homogeneous liquids comprising a solution of the reactants and catalyst component in an inert solvent such as acetic acid. Thus, the crude, liquid product obtained from such acetic anhydride processes typically comprises a mixture of acetic anhydride and acetic acid as a result of the use of acetic acid as a process solvent. Acetic acid may be coproduced in the process by feeding methanol and/or water to the production system, e.g., by feeding methanol and/or water to a process recycle stream containing acetic anhydride and/or to the carbonylation reactor.

The above-described processes for the manufacture of acetic anhydride are carried out by feeding carbon monoxide to a reaction zone containing a liquid mixture of (i) a reactant compound selected from methyl acetate, dimethyl ether or a mixture thereof, (ii) methyl iodide and (iii) catalyst components comprising rhodium and one or more promoters. The carbon monoxide is fed below the surface of the liquid mixture in a finely divided form, e.g., by means of a gas sparging device, to maximize the concentration of carbon monoxide in the reaction mixture. Normally, the process is operated by feeding continuously the reactant compound, methyl iodide, an inert solvent such as acetic acid, and catalyst components dissolved in acetic anhydride and/or acetic acid and carbon monoxide to a reaction zone and removing continuously from the reaction zone a crude product mixture comprising acetic anhydride and acetic acid. The crude product mixture also contains reactant compound, methyl iodide, acetic acid solvent and catalyst components and carbon monoxide dissolved in the crude product. The crude product is fed continuously to a first separation zone wherein the pressure is reduced and the crude product flash distilled to produce (i) a vapor effluent comprising reactant compound, methyl iodide, acetic acid solvent, acetic anhydride product and carbon monoxide and (ii) a liquid effluent comprising the catalyst components dissolved in a mixture of acetic anhydride and acetic acid. The vapor effluent typically comprises about 30 to 90 weight percent of the crude product fed to the first separation zone. The liquid effluent is recycled to the reaction zone and the vapor effluent is fed to a product recovery zone wherein the acetic anhydride (and any coproduced acetic acid) is separated and removed from the production system. The other condensible components (methyl acetate, methyl iodide and acetic acid solvent) are recovered and recycled to the reaction zone.

The carbon monoxide contained in the crude product mixture can be recovered only at great expense. For example, carbon monoxide recovery by recompression and recycle of the purged gas is not desirable because the inert impurity components of the recovered gas, e.g., hydrogen, methane, carbon dioxide, nitrogen and argon, build up in the reaction system and reduce carbon monoxide partial pressure. Removal of the impurities from the carbon monoxide involves complex, capital-intensive processes such as cryogenic distillation, adsorption, or membrane separators followed by recompression. The capital cost of equipment for the purification and recompression of the discharged carbon monoxide exceeds the value of the carbon monoxide. Consequently, the carbon monoxide contained in the vapor effluent from the first separation zone typically is not recovered and is lost from the process at significant expense. The carbon monoxide which is not recovered can constitute up to 10 volume percent of the total carbon monoxide fed to the reaction zone. If the carbon monoxide is not recovered, the gaseous effluent either must be treated or burned. Thus, an economical means for the utilization of the carbon monoxide present in the crude reaction product would improve the overall economics of the process.

An acetic anhydride manufacturing process now has been developed whereby the utilization of carbon monoxide has been increased, thus increasing the overall production and yield of acetic anhydride (and any acetic acid coproduced) produced per unit of carbon monoxide fed to the carbonylation process. The present invention therefore provides a liquid phase process for the manufacture of acetic anhydride under substantially anhydrous conditions which comprises the steps of:

(1) continuously feeding to a first reaction zone (i) a reactant compound selected from methyl acetate, dimethyl ether or a mixture thereof, (ii) methyl iodide, (iii) dissolved catalyst components comprising rhodium and one or more promoters, (iv) acetic acid solvent, and (v) carbon monoxide, wherein the carbon monoxide is fed below the surface of the liquid reaction mixture comprising components (i), (ii) and (iv) and the reactant compound is converted to acetic anhydride to produce a first liquid reaction mixture comprising (i) a reactant compound selected from methyl acetate, dimethyl ether or a mixture thereof, (ii) methyl iodide, (iii) dissolved catalyst components comprising rhodium and one or more promoters, (iv) acetic acid solvent, (v) dissolved carbon monoxide and (vi) acetic anhydride product;

(2) removing the first liquid reaction mixture from the first reaction zone and feeding it to a second reaction zone comprising at least one reaction vessel in which is maintained a liquid phase comprising the first liquid reaction mixture and an overhead vapor phase wherein a carbon monoxide partial pressure of about 10 to 30 bar absolute (bara) is maintained, no carbon monoxide is fed below the surface of the liquid phase, and the residence time of the liquid phase in the second reaction zone is at least 2 minutes, preferably from about 4 to 10 minutes, to produce a second liquid reaction mixture comprising (i) a reactant compound selected from methyl acetate, dimethyl ether or a mixture thereof, (ii) methyl iodide, (iii) dissolved catalyst components comprising rhodium and one or more promoters, (iv) acetic acid solvent, (v) dissolved carbon monoxide and (vi) acetic anhydride product; and (3) removing the second liquid reaction mixture from the second reaction zone;

whereby the utilization of carbon monoxide in the process is increased, i.e., the concentration of carbon monoxide in the second liquid reaction mixture is less than the concentration of carbon monoxide in the first liquid reaction mixture. Typically, the concentration of carbon monoxide in the second liquid reaction mixture is about 50 volume percent or less, preferably about 5 to 50 volume percent, of the carbon monoxide concentration in the first liquid reaction mixture. U.S. Pat. No. 5,672,744 pertains to a process for the preparation of acetic acid comprising the steps of:

(1) carbonylating methanol with carbon monoxide in a first reactor in the presence of a reaction fluid comprising a rhodium catalyst, methyl iodide, an iodide salt, methyl acetate and water;

(2) withdrawing a reaction fluid having carbon monoxide dissolved therein from the first reactor and introducing it into a second reactor;

(3) carbonylating methanol in the second reactor with the carbon monoxide dissolved in the reaction fluid at a residence time of from 7 to 30 seconds and a temperature of from 150 to 220° C. and forming a crude acetic acid mixture; and (4) introducing the crude acetic acid mixture into a flash zone to separate it into a vapor phase and a liquid phase.

U.S. Pat. No. 5,672,744 does not contemplate a process for manufacturing acetic anhydride under substantially anhydrous conditions using a residence time in the second reactor or reaction zone of at least 2 minutes. Furthermore, the '744 patent does not disclose the importance of using the particular reaction system used in the second reaction zone of the process of the present invention.

The process of the present invention is an improvement of the rhodium-catalyzed, carbonylation processes described in the literature such as the patent publications referred to above. Thus, our novel process may be carried out by continuously feeding to a first reaction zone (i) a reactant compound selected from methyl acetate, dimethyl ether or a mixture thereof, (ii) methyl iodide, (iii) dissolved catalyst components comprising rhodium and one or more promoters, (iv) acetic acid solvent, and (v) carbon monoxide wherein the carbon monoxide is fed below the surface of the liquid reaction medium. The feed to the carbonylation zone also may include methanol and/or water to co-produce acetic anhydride and acetic acid as described in Published European Patent Applications 87,869 and 87,870. The process of the present invention is operated under substantially anhydrous conditions, i.e., under steady state operating conditions water either cannot be detected or can be detected only in trace amounts. Any water fed to the process is fed in an amount which significantly less than the amount necessary to convert all of the acetic anhydride to acetic acid.

The first reaction zone may comprise one or more pressure vessels which may be provided with means for agitation. The vessel design may be a pipe reactor, column, tank, stirred tank or other design. It is preferred that the first reaction zone comprises at least one generally columnar vessel equipped with one or more internal baffles which, in combination with the carbon monoxide gas sparger feed device, create a highly agitated, recirculating reaction mixture. The residence time of the reactant within the first reaction zone normally is at least 20 minutes and, preferably, is in the range of about 30 to 50 minutes.

The reactant compound, methyl iodide and carbon monoxide react in the first reaction zone to form acetic anhydride to produce a first liquid reaction mixture comprising (i) a reactant compound selected from methyl acetate, dimethyl ether or a mixture thereof, (ii) methyl iodide, (iii) dissolved catalyst components comprising rhodium and one or more promoters, (iv) acetic acid solvent, (v) dissolved carbon monoxide and (vi) acetic anhydride product. This first reaction mixture is fed to a second reaction zone comprising at least one reaction vessel which contains a liquid phase comprising the first liquid reaction mixture and an overhead vapor phase. The vessel(s) constituting the second reaction zone may be of a columnar or tank design and may be equipped with means for agitating the liquid phase contained therein. An unagitated plug flow reactor is preferred since carbon monoxide depletion is greater for plug flow design versus a stirred tank reactor design.

By controlling the total pressure and liquid level in the second reaction zone, the amount of carbon monoxide that is depleted from the first liquid reaction mixture can be controlled to a predetermined level in order to avoid total or near total depletion, resulting in possible deleterious effects to the catalytically-active rhodium complex and its solubility in the reaction mixture. It is an important practical design feature to maintain a reactor liquid level with an overhead vapor space such that the vapor space is approximately 5 to 30% of the total reactor volume. This design feature provides a compressible gas cushion in the event that the reactor is "bottled up". If bottling up occurs, temperature will increase as the reaction of dissolved carbon monoxide goes to completion and a volume expansion of the reactor liquid will occur. With the presence of a gas cushion, the gas will be compressed rather than having a hydraulic relief of the reactor.

The total pressure within the second reaction zone is approximately equal to the total pressure in the first reaction zone and preferably is in the range of about 30 to 50 bara. Carbon monoxide may be fed to the vapor space of the second reaction zone to maintain the gas cushion and the desired total reaction pressure. This may be necessary since the liquid at the top of the reactor comprising the second reaction zone will be considerably below the saturation limit of carbon monoxide (since dissolved carbon monoxide will have reacted) and carbon monoxide from the vapor space will diffuse from the gas into the liquid. Additional production may be achieved from the added carbon monoxide as well as from the dissolved carbon monoxide. No carbon monoxide is fed below the surface of the liquid phase in the second reaction zone.

The residence time of the liquid phase in the second reaction zone is at least 2 minutes, preferably from about 4 to 10 minutes. The reactant compound, methyl iodide and carbon monoxide dissolved in the first reaction mixture react in the second reaction zone to produce additional acetic anhydride, thereby lowering the concentration of carbon monoxide in the liquid phase. The first reaction mixture usually contains sufficient reactant compound to react with and consume carbon monoxide in the second reaction zone.

The reactant compound typically is present in a concentration of at least 5, preferably in a concentration in the range of about 20 to 40, weight percent based on the total weight of the first reaction mixture. If necessary or desired, additional reactant compound can be added to the second reaction zone.

The second liquid reaction mixture comprising (i) a reactant compound selected from methyl acetate, dimethyl ether or a mixture thereof, (ii) methyl iodide, (iii) dissolved catalyst components comprising rhodium and one or more promoters, (iv) acetic acid solvent, (v) dissolved carbon monoxide and (vi) acetic anhydride product formed is removed from the second reaction zone and fed to a separation zone wherein the product acetic anhydride and any coproduced acetic acid are recovered. As mentioned previously, the concentration of carbon monoxide in the second liquid reaction mixture is about 50 volume percent or less, preferably about 5 to 50 volume percent, of the carbon monoxide concentration in the first liquid reaction mixture.

In a preferred mode of operation, the conversion of reactant compound and methyl iodide components of the first liquid reaction mixture may be maximized by feeding the mixture in a finely divided form, e.g., as a spray or turbulent liquid, to the gaseous space of the second reaction zone. The second liquid reaction mixture is withdrawn from the opposite end (bottom) of the second reaction zone. This mode of operation results in increased uptake or consumption of carbon monoxide in the gaseous space and thus increased production of acetic anhydride while achieving the primary objective of reducing the dissolved carbon monoxide in the first liquid reaction mixture.

The reaction zones are maintained at elevated temperature and pressure (total) such as 100 to 300° C. and 21.7 to 276.7 bara (300 to 4000 pounds per square inch gauge—psig) although temperatures and total pressures in the range of 175 to 220° C. and 35.5 to 104.4 bara (500 to 1500 psig) are more common. Typically, the reaction of dissolved carbon monoxide in the second reaction zone is allowed to occur adiabatically resulting in a slight temperature increase, e.g., up to about 5° C. The gas fed to the carbonylation zone may consist of essentially carbon monoxide or a mixture of carbon monoxide and hydrogen, e.g., a mixture of carbon monoxide and up to 7 volume percent hydrogen.

The rhodium component of the catalyst system may be provided to the process in various forms such as rhodium trichloride or triiodide, rhodium hydrate, or rhodium carbonyl complexes, e.g., $[Rh(CO)_2I]_2$ from which the soluble, catalytically-active rhodium complex is formed. See, for example, the catalyst description in U.S. Pat. No. 4,374,070 and Roth et al., Chem. Tech., 1971 p. 600. The rhodium concentration in the liquid mixtures contained in the reaction zones may be from 250 to 1300 ppm although concentrations of 400 to 1000 ppm typically are used.

The promoter component of the catalyst system may be (1) an inorganic iodide salt such as lithium iodide or an iodide salt of a quaternary organophosphorus or organonitrogen compound or (2) an inorganic compound or an organophosphorus or organonitrogen compound which forms an iodide salt in the carbonylation zone. The organophosphorus or organonitrogen iodides may be selected from phosphonium iodides, ammonium iodides and heterocyclic aromatic compounds in which at least one ring hetero atom is a quaternary nitrogen atom. Examples of such phosphorus- and nitrogen-containing iodides include tetra(hydrocarbyl)phosphonium iodides such as tributyl(methyl) phosphonium iodide, tetrabutylphosphonium iodide, tetraoctylphosphonium iodide, triphenyl(methyl)phosphonium iodide, tetraphenylphosphonium iodide and the like; tetra(hydrocarbyl)ammonium iodides such as tetrabutylammonium iodide and tributyl(methyl)ammonium iodide; and heterocyclic aromatic compounds such as N-methylpyridinium iodide, N,N'-dimethylimidazolium iodide, N-methyl-3-picolinium iodide, N-methyl-2,4-litidinium iodide, N-methyl-2,4-lutidinium iodide and N-methylquinolinium iodide. The preferred iodide salt promoters comprise lithium iodide and tetraalkylphosphonium iodides, triphenyl(alkyl)phosphonium iodides, tetraalkylammonium iodides and N,N'-dialkylimidazolium iodides wherein the alkyl groups contain up to 8 carbon atoms.

A portion or all of the promoter compound may be fed as a compound which forms an iodide salt in the carbonylation zone. Thus, the promoter compounds may be fed initially in the form of their corresponding acetates, hydroxides, chlorides or bromides or the phosphorus- and nitrogen-containing promoters may be fed as compounds in which the phosphorus or nitrogen atoms are trivalent, e.g., tributylphosphine, tributylamine, pyridine, imidazole, N-methylimidazole and the like, which are quaternized by the methyl iodide present in the carbonylation zone.

The amount of the iodide salt promoter present in the carbonylation zone can be varied substantially depending on a variety of factors, especially on the particular promoter used. For example, the concentration of lithium iodide in the reaction mixture may range from 175 to 5000 ppm Li, preferably 1500 to 3700 ppm Li, whereas the phosphorus- and nitrogen-containing promoters may be present in concentrations of 0.5 to 25 weight percent, calculated as their iodide salts and based on the total weight of the reaction mixture, i.e., the contents of the carbonylation zone. The amounts of other materials, e.g., acetic acid, acetic anhydride, methyl iodide, methyl acetate and/or dimethyl ether present in the reaction mixture vary substantially depending, for example, on the carbonylation rate, residence time and concentrations of the iodide salt promoter and acetic acid solvent.

An effluent is continuously removed from the carbonylation zone and separated into a major vapor fraction comprising methyl iodide, methyl acetate and/or dimethyl ether, acetic acid and acetic anhydride and a minor fraction comprising a solution of catalyst components in a mixture of acetic acid and acetic anhydride. The minor fraction is recycled to the carbonylation zone and the major fraction is separated by a series of distillations into its component parts.

The process of the present invention is further illustrated by the following example wherein the amounts of materials are given in parts per weight unless otherwise stated. Percentages are by weight unless otherwise stated.

The following materials are fed continuously at the rates shown to a first reaction zone comprising one or more baffled, back-mixed reaction vessel to which carbon monoxide is fed below the surface of the reaction mixture by means of a gas sparger device at the rate 560 parts per minute:

Methyl acetate 2466 parts per minute
Methyl iodide 704 parts per minute
Acetic acid 1269 parts per minute
Acetic anhydride 585 parts per minute Rhodium and lithium catalyst components are fed as a solution in the acetic acid/acetic anhydride feed and give a concentration of 400 to 1000 ppm [Rh] and 1000 to 2500 ppm [Li] in the liquid mixture contained in the first reaction zone. The capacity of the first reaction zone is designed to give a residence time of approximately 40 minutes. A temperature of about 190 to 210° C. and a total pressure of about 40 to 50 bara are maintained in the first reaction zone.

A first liquid reaction mixture is withdrawn continuously from the first reaction zone at a rate of approximately 5570 parts per minute and fed to the vapor space of a second reaction zone comprising a tank reaction vessel to which carbon monoxide is fed to the vapor space at the top. The composition of the first liquid reaction mixture is approximately 30% methyl acetate, 12% methyl iodide, 22% acetic acid, 29% acetic anhydride and 0.7 volume % carbon monoxide. Approximately 7% of the first liquid reaction mixture consists of other components such as ethylidene diacetate, tar, acetone, inert materials, etc. Carbon monoxide is supplied to the vapor space of the second reaction zone to maintain a total pressure of about 40 to 50 bara. The residence time within the second reaction zone is approximately 4 to 6 minutes. The amount of carbon monoxide supplied to the second reaction zone is about 20 parts per minute. A temperature of about 190 to 210° C. and a total pressure of about 40 to 50 bara are maintained in the second reaction zone.

A second liquid reaction mixture is removed continuously from the bottom of the second reaction zone at a rate of 5590 parts per minute and fed to a first separation zone wherein the pressure is reduced to 2 to 5 bara to flash distill approximately 80% of the feed mixture. The composition of the second liquid reaction mixture is approximately 29% methyl acetate, 12% methyl iodide, 22% acetic acid, 31% acetic anhydride, 0.2% carbon monoxide and about 7% other materials. That portion of the second liquid reaction mixture not vaporized comprises about 37% acetic acid, 45% acetic anhydride, the rhodium and lithium catalyst components and tar and other high boilers. Approximately 70% of the carbon monoxide dissolved in the first liquid reaction mixture was reacted in the second reaction zone. This increased the overall utilization of carbon monoxide from about 90% to about 95%.

The invention has been described in detail with particular reference to preferred embodiments thereof, but it will be understood that variations and modifications can be effected within the spirit and scope of the invention.

We claim:

1. Process for the manufacture of acetic anhydride in the liquid phase under substantially anhydrous conditions which comprises the steps of:
   (1) continuously feeding to a first reaction zone (i) a reactant compound selected from methyl acetate, dimethyl ether or a mixture thereof, (ii) methyl iodide, (iii) dissolved catalyst components comprising rhodium and one or more promoters, (iv) acetic acid solvent, and (v) carbon monoxide, wherein the carbon monoxide is fed below the surface of the liquid reaction mixture comprising components (i), (ii) and (iv) and the reactant compound is converted to acetic anhydride to produce a first liquid reaction mixture comprising (i) a reactant compound selected from methyl acetate, dimethyl ether or a mixture thereof, (ii) methyl iodide, (iii) dissolved catalyst components comprising rhodium and one or more promoters, (iv) acetic acid solvent, (v) dissolved carbon monoxide and (vi) acetic anhydride product;
   (2) removing the first liquid reaction mixture from the first reaction zone and feeding it to a second reaction zone comprising at least one reaction vessel in which is maintained a liquid phase comprising the first liquid reaction mixture and an overhead vapor space wherein a total pressure of about 40 to 50 bar absolute (bara) is maintained, no carbon monoxide is fed below the surface of the liquid phase, and the residence time of the liquid phase in the second reaction zone is at least 2 minutes to produce a second liquid reaction mixture comprising (i) a reactant compound selected from methyl acetate, dimethyl ether or a mixture thereof, (ii) methyl iodide, (iii) dissolved catalyst components comprising rhodium and one or more promoters, (iv) acetic acid solvent, (v) dissolved carbon monoxide and (vi) acetic anhydride product; and
   (3) removing the second liquid reaction mixture from the second reaction zone;
   whereby the utilization of carbon monoxide in the process is increased.

2. Process according to claim 1 wherein the concentration of carbon monoxide in the second liquid reaction mixture is about 5 to 50 volume percent of the carbon monoxide concentration in the first liquid reaction mixture.

3. Process according to claim 1 wherein the process is carried out at a temperature of about 100 to 300° C. and a pressure (total) of about as 21.7 to 276.7 bara and the residence time within the second reaction zone is about 4 to 20 minutes.

4. Process according to claim 1 wherein the process is carried out at a temperature of about 175 to 220° C. and a pressure (total) of about as 35.5 to 104.4 bara, the residence time within the second reaction zone is about 4 to 10 minutes, and the second liquid reaction mixture fed to the second reaction zone comprises about 20 to 40 weight percent methyl acetate.

5. Process for the manufacture of acetic anhydride in the liquid phase under substantially anhydrous conditions at a temperature of about 175 to 220° C. and a pressure (total) of about as 35.5 to 104.4 bar absolute (bara) which comprises the steps of:
   (1) continuously feeding to a first reaction zone (i) a reactant compound selected from methyl acetate, dimethyl ether or a mixture thereof, (ii) methyl iodide, (iii) dissolved catalyst components comprising rhodium and one or more promoters, (iv) acetic acid solvent, and (v) carbon monoxide, wherein the carbon monoxide is fed below the surface of the liquid reaction mixture comprising components (i), (ii) and (iv) and the reactant compound is converted to acetic anhydride to produce a first liquid reaction mixture comprising (i) a reactant compound selected from methyl acetate, dimethyl ether or a mixture thereof, (ii) methyl iodide, (iii) dissolved catalyst components comprising rhodium and one or more promoters, (iv) acetic acid solvent, (v) dissolved carbon monoxide and (vi) acetic anhydride product;
   (2) removing the first liquid reaction mixture from the first reaction zone and feeding it in a finely divided form to the vapor space of a second reaction zone comprising at least one reaction vessel in which is maintained a liquid phase comprising the first liquid reaction mixture and an overhead vapor space wherein a total pressure of about 40 to 50 bara is maintained, carbon monoxide is fed to the vapor space, no carbon monoxide is fed below the surface of the liquid phase, and the residence time of the liquid phase in the second reaction zone is at least 2 minutes to produce a second liquid reaction mixture comprising (i) a reactant compound selected from methyl acetate, dimethyl ether or a mixture thereof, (ii) methyl iodide, (iii) dissolved catalyst components comprising rhodium and one or more promoters, (iv) acetic acid solvent, (v) dissolved carbon monoxide and (vi) acetic anhydride product; and
   (3) removing the second liquid reaction mixture from the second reaction zone;
   wherein the concentration of carbon monoxide in the second liquid reaction mixture is about 5 to 50 volume percent of the carbon monoxide concentration in the first liquid reaction mixture.

6. Process according to claim 5 wherein the residence time within the second reaction zone is about 4 to 10 minutes and the second liquid reaction mixture fed to the second reaction zone comprises about 20 to 40 weight percent methyl acetate.

* * * * *